United States Patent [19]

Fried

[11] Patent Number: 4,705,505
[45] Date of Patent: Nov. 10, 1987

[54] RAPID SOLUTION ADMINISTRATION SET WITH INTEGRAL HEAT EXCHANGER

[76] Inventor: Steven J. Fried, 1729 Willow Park Ct., Powell, Ohio 43065

[21] Appl. No.: 930,739

[22] Filed: Nov. 13, 1986

Related U.S. Application Data

[63] Continuation of Ser. No. 655,379, Sep. 28, 1985, Pat. No. 4,623,333.

[51] Int. Cl.$^4$ .............................................. A61M 5/14
[52] U.S. Cl. ........................................ 604/80; 604/82; 604/113; 604/122
[58] Field of Search ................. 604/4, 53, 80, 82, 122, 604/252, 113; 128/400, 399

[56] References Cited

U.S. PATENT DOCUMENTS

| | | | |
|---|---|---|---|
| 4,177,816 | 12/1979 | Torgeson | 128/400 |
| 4,416,280 | 11/1983 | Carpenter et al. | 604/4 |
| 4,476,877 | 10/1984 | Barker | 604/53 |
| 4,479,798 | 10/1984 | Parks | 604/4 |
| 4,493,705 | 1/1985 | Gordon et al. | 604/4 |

OTHER PUBLICATIONS

Millikan, et al, "Rapid Volume Replacement for Hypovolemic Shock: A Comparison of Techniques and Equipment," *The Journal of Trauma*, vol. 24, No. 5, 1984.

Fried, et al. "Normothermic Rapid Volume Replacement for Hypovolemic Shock: An in vivo and in vitro Study Utilizing a New Technique", *The Journal of Trauma*, vol. 26, No. 2, 1986.

*Primary Examiner*—C. Fred Rosenbaum
*Assistant Examiner*—Sherri Vinyard
*Attorney, Agent, or Firm*—Wolf, Greenfield & Sacks.

[57] ABSTRACT

Apparatus for the rapid infusion of physiologic solutions into the human body which have been warmed by said apparatus to normothermic temperature. The apparatus includes an extracorporeal heat exchanger which warms cold bank blood and other physiologic solutions to normothermic temperature. Bank blood and blood products enter the apparatus through a filtered infusion line. Crystalloids and synthetic colloids enter the apparatus through an unfiltered infusion line. Bank blood, blood products, crystalloids, and synthetic colloids flow through PVC tubing, filtered drip chambers, and the extracorporeal heat exchanger at a rapid rate to restore and maintain the normal circulating blood volume of a patient in hypovolemic shock. The flow rate is regulated by PVC tube clamps and a fluid shut-off valve. The apparatus also embodies a macrodrip administration set for the infusion of drugs and other physiologic solutions at a slower infusion rate. Normothermic physiologic solutions are infused into the patient's central venous blood pathway through a large-bore vein catheter.

14 Claims, 2 Drawing Figures

RAPID SOLUTION ADMINISTRATION SET WITH INTEGRAL HEAT EXCHANGER

BACKGROUND OF THE INVENTION

Related Application

This application is a continuation of my earlier application Ser. No. 06/655,379 filed Sept. 28, 1985, now U.S. Pat. No. 4,623,333 dated Nov. 18, 1986.

FIELD OF THE INVENTION

The present invention relates to the treatment of human subjects for hypovolemic shock by rapid infusion of physiologic solutions such as crystalloid solutions, colloid solutions, packed red blood cells and whole blood into the human body, which have been warmed to normothermic temperature prior to their infusion into the human body.

DESCRIPTION OF THE PRIOR ART

Treatment of hypovolemic shock requires rapid volume replacement and maintenance of physiologic solutions as well as the maintenance of normothermic temperature in vital organs of the human body. In order to resuscitate a victim in a hypovolemic shock, secondary to traumatic or intraoperative hemorrhage, physiologic solution including blood products, synthetic colloids, and crystalloids must be rapidly infused into the body. These physiologic solutions are presently introduced through a multitude of venipunctures cannulated with 18-gauge or larger internal diameter catheters. The rapidly infused physiologic solutions should also be warmed to normothermic temperature in order to maintain normothermic temperatures in the vital organs of the body and prevent transfusion-induced hypothermia. Present methods of fluid administration achieve infusion rates which are too slow. Present blood warming methods demonstrate an inherent resistance to infusion flow, which does not allow adequate flow rates for optimal hypovolemic shock treatment.

Banked blood is stored in a refrigerated environment at a temperature of 4° Centigrade. For years, banked blood has been transfused into human subjects cold as it came from the storage refrigerator. Patients who receive as little as two units of cold banked blood tend to become hypothermic. The first major organ to be exposed to the stream of cold bank blood is the heart. Heart rate, blood pressure, cardiac output, and coronary blood flow all fall progressively as body temperature drops. The heart tends to fail during cooling either suddenly because of ventricular fibrillation, or gradually because of ischemia. C. P. Boyan, "Cold or Warmed Blood for Massive Transfusions." *Annals of Surgery*, 160: 282–286 (1964). In a study of 154 hypovolemic shock victims, Dr. Boyan found that there was a 58 percent mortality rate among patients receiving cold infusion of resuscitation fluids. There was a 6 percent mortality rate among patients receiving normothermic massive transfusions. Id. at pp. 284–286. However, the volume replacement system used in that study was deficient due to its large priming volume requirement, its lack of controlled warming capability, and its less than optimal infusion delivery rate.

Fluid replacement through peripheral veins has been the standard method of volume resuscitation. Cold bank blood and blood products are infused into the patient through a "Y" type blood solution administration set. The blood solution administration set uses a 200 micron filter and PVC tubing which is 84 inches long and has 0.06 inch internal diameter. A crystalloid solution administration set is sometime used. It employs PVC tubing which is 93 inches long and has 0.06 internal diameter. A 16-gauge vein catheter is attached to each blood or crystalloid solution administration set, and is inserted directly into the vein. Fluids are kept in storage bags which are elevated above the solution administration sets. Each solution administration set has a hollow spike connector, which is used to connect it to the storage bag. Gravity induces the fluid to flow from the storage bag through the spike connector into the solution administration sets. The solution administration sets are elevated above the patient, and gravity induces the fluid to flow through the sets to the attached vein catheters. Fluid then enters the patient through the catheter into the venous access sites.

Certain disadvantages are inherent in the use of solution administration sets to infuse cold bank blood and blood products for volume resuscitation. First, it is likely that the patient will experience transfusion-induced hypothermia. Rapid body cooling during the treatment of hypovolemic shock is associated with cardiac arrest. Second, the PVC tubing used in prior fluid administration resists flow and delays delivery of fluid to central compartments. Tubing which a 0.06 inch internal diameter, and which a long length of 84 inches or more, cannot deliver fluids to a patient at an infusion rate needed for successful resuscitation from hypovolemic shock. The infusion rate of replacement fluids to the patient may not approximate the rate of loss. Unless such an infusion rate is achieved, the patient cannot be resuscitated. Also, in a hypotensive, hypovolemic shock victim, peripheral veins are not always easily accessible for multiple venipunctures. J. Scott Millikan, Thomas L. Cain, and John Hansbrough, "Rapid Volume Replacement for Hypovolemic Shock: A Comparison of Techniques and Equipment." Journal of Trauma, 24: 428–431 (1984). This procedure requires multiple venous access sites to connect several infusion systems for adequate volume replacement. Initiating such treatment is time consuming, and the delay incurred contributes significantly to the mortality rate among hypovolemic shock victims. During the time taken to initiate treatment, physiologic alterations produced by massive hemorrhage progress to an irreversible state, making death inevitable.

A fluid warming coil is used in volume resuscitation. A device of this type is described and illustrated in U.S. Pat. No. 3,472,369 to Samuel J. Schuster. The fluid warming coil described in the Schuster patent consists of PVC tubing which is 34 feet long. It also has a 0.06 inch internal diameter. The device described in the Schuster patent must also be immersed in a tank of warm water for heat transfer. Cold bank blood and blood products are warmed by flowing through the plastic tubing after it has been immersed in warm water.

Certain disadvantages are inherent in the device described in the patent. First, it does not allow measurement of blood temperature. It therefore does not facilitate controlled warming of cold blood and blood products to normothermic temperature. Controlled warming is critical in the prevention of hypothermia, or of hyperthermia which may cause red blood cell hemolysis and platelet denaturation and can thereby cause death. Second, the coil length and internal diameter resists blood flow such that the coil cannot warm blood at maximal infusion rates of 1500 milliliters per minute or greater. Use of the coil where massive hemorrhage has occurred therefore reduces the patient's likelihood of resuscitation from hypovolemic shock.

Consequently, a need exists for improvements in the infusion of normothermic physiologic solutions into human subjects experiencing hypovolemic shock.

SUMMARY OF THE INVENTION

The present invention embodies an apparatus for rapid fluid replacement and controlled warming of physiologic solutions. It is an intravenous set which uses 0.25 inch internal diameter PVC tubing to infuse physiologic solutions into the central venous blood pathway through an attached vein catheter. The vein catheter must have an internal diameter of at least 14-gauge. The present invention embodies larger-bore PVC tubing than prior solution administration sets. It embodies a single larger-bore vein catheter than vein catheters used in prior solution administration sets. The present invention can infuse phsyiologic solutions such as crystalloids and certain blood products into a patient at the flow rates in the range of 800 milliliters per minute to 1500 milliliters per minute or greater, which exceeds the flow rate of prior solution administration sets. The length of the present invention is only 70 inches, thereby facilitating the faster flow rate.

The preferred embodiment of the present invention includes an ancillary macrodrip administration set for the infusion of drugs and physiologic solutions at a rate slower than the infusion of bank blood, blood products, colloids, and crystalloids through the rapid solution administration set. No prior blood or crystalloid administration set incorporates ancillary macrodrip administration.

The present invention also includes a rapid fluid warmer of the type described and illustrated in U.S. Pat. No. 4,177,816 to William Torgeson. The device described in the Torgeson patent has not previously been incorporated in an apparatus for treatment of hypovolemic shock. The device described in the Torgeson patent permits rapid, controlled warming of fluids. The present invention permits the measuring of fluid temperature before entering and after exiting the device described in the Torgeson patent. Accordingly, the warming of fluids by the device described in the Torgeson patent can be monitored and adjusted to maintain normothermic temperature, and prevent excessive warming.

The device described in the Torgeson patent is only 20 inches long. Its length and the size of its heating surface area is such that this device can warm blood at a flow rate of 1500 milliliters per minute or greater.

Figure 1A:
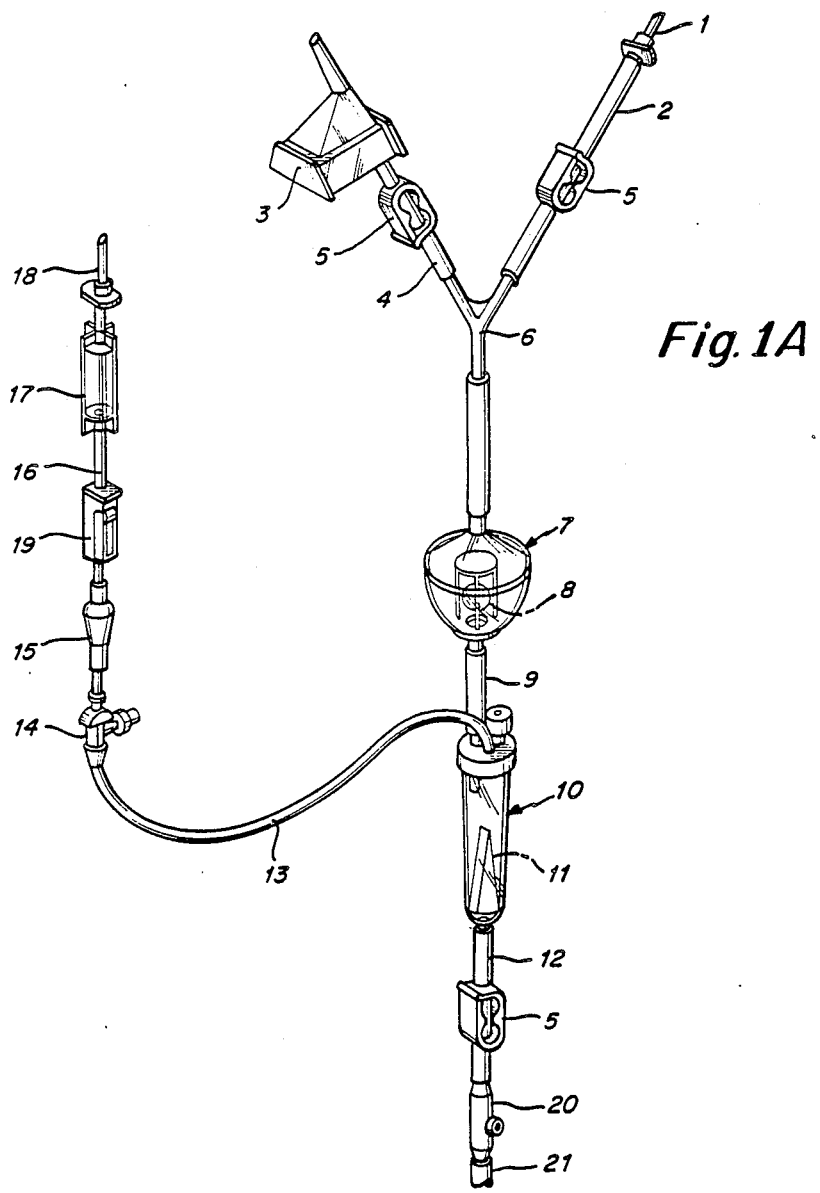
FIG. 1a is a perspective view of the upper section of the present invention.
Figure 1B:
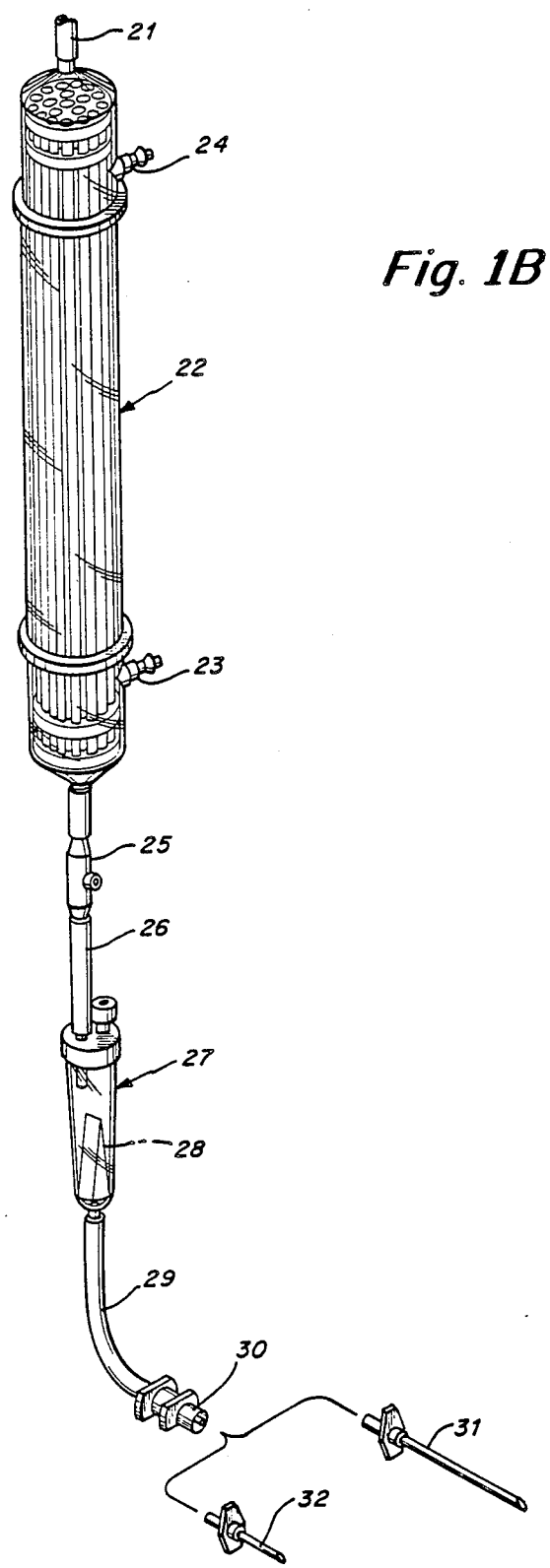
FIG. 1b is a perspective view of the lower section of the present invention.

The drawings of FIGS. 1a and 1b form, in effect, a single complete figure. The drawings should be arranged so that the bottom of FIG. 1a is adjacent to the top of FIG. 1b.

DESCRIPTION OF THE PREFERRED EMBODIMENT

To successfully treat a patient in hypovolemic shock the system used must be capable of rapidly restoring the lost blood volume of the patient. The system must also have the capability of maintaining the normovolemic status by introducing physiologic solution at a rate equal to the ongoing blood loss. Preferably, the system is also capable of being controlled so as to reduce the infusion flow rates as the rate of blood loss dissipates.

The physiologic solution introduced by the system can take one of several forms. In the course of treatment any one or a combination of solutions may be administered. Frequently, the most readily available initial solution used is a crystalloid solution which has a low viscosity and is stored at room temperature. The present invention is capable of infusing that solution at approximately 1500 milliliters per minute. Other solutions frequently used are blood products deficient in red blood cells, e.g. albumin, plasma and platelets. These solutions are normally introduced into the system at room temperature and have a viscosity similar to crystalloids, thus allowing flow rates of approximately 1500 milliters per minute. A third solution is whole blood, which is a combination of red blood cells, platelets and plasma. This solution has a slightly greater viscosity than the above mentioned solutions, is introduced to the system at approximately 4° C. and may be infused by the system of this invention at approximately 1000 milliliters per minute. A fourth solution is packed red blood cells, which has a substantially higher viscosity than the others, is introduced to the system at approximately 4° C., and can be infused by the system of this invention at a rate of approximately 800 milliliters per minute.

Referring now to the drawings, and more particularly to FIG. 1a, there is shown the most proximal end of the rapid solution administration set. The fluid connector spike 1 is a rigid, molded plastic spike connecting the desire infusate solution bag to a six inch long, 0.25 inch internal diameter PVC tube comprising a non-filtered infusion line 2. The blood transfusion filter 3 is a disposable, interchangeable, free-flow 40 micron pore size screen filter with a molded plastic spike. This low priming volume filter performs microaggregate filtration. It connects the desired infusion solution bag to a three inch long, 0.25 inch internal diameter PVC tube, and comprises the filtered infusion line 4. Located around the filtered infusion line 2, the non-filtered line 4, and distally around 0.25 inch internal diameter PVC tubing 12 are plastic tube clamps 5. The clamps regulate gravity-induced infusate flow. When closed, the tube clamps 5 occlude the PVC tubing within each clamp and restrict the flow of infusate solution. When the clamps are opened, the PVC tubing allows free flow of the infusate solution. Each tube clamp 5 functions independently, and provides selective fluid flow for specific physiologic solutions required in rapid volume replacement. When the filtered infusion line 4 and the non-filtered infusion line 2 are connected to infusate solution bags, the tube clamps 5 are closed until infusion is initiated.

The filtered and non-filtered infusion lines are joined by a 0.25 inch internal diameter plastic "Y" connector 6 to form a common infusion line. The "Y" connector 6 is 0.25 inch internal diameter rigid plastic connector, which is three inches in length. The "Y" connector 6 is connected to a fluid shut-off valve 7. When placed with its axial centerline at or near the vertical position, the fluid shut-off valve 7 will seal and stop the flow of air at its distal outlet. When primed with fluid, the hollow ball 8 within the fluid shut-off valve 7 floats freely. The hollow ball 8 is supported by hydrostatic and hydrodynamic force during fluid flow. If air enters the fluid shut-off valve 7, the ball sinks and occludes the distal outlet, thereby terminating fluid flow. To reopen the fluid shut-off valve 7, fluid must be introduced retrograde into the valve, unseating the hollow ball 8. The present invention embodies the fluid shut-off valve 7 to prevent introduction of an air bolus into the patient.

At the distal outlet of the fluid shut-off valve 7, a 1.5 inch length of 0.25 inch internal diameter PVC tubing 9 connects to a 170 micron pore size filtered drip chamber 10. The 170 micron pore size filtered drip chamber 10 is a pliable plastic reservoir containing a 170 micron mesh filter 11 within. It functions as a gross microaggregate filter, and as a means of facilitating retrograde flow to reprime the fluid shut-off valve 7. After changing the emptied infusate bag and clamping the PVC tubing 12 on the distal outlet of the filtered drip chamber 10, the system may be reprimed by squeezing the filtered drip chamber 10. Fluid will be displaced out of the proximal inlet of the filtered drip chamber 10, causing retrograde filling of the fluid shut-off valve 7.

The proximal inlet cap of the filtered drip chamber 10 is attached to an ancillary macrodrip administration set through a 0.06 inch internal diameter ancillary infusion line 13. It provides a means for drug introduction at slower drip rates into the present invention. The ancillary infusion line 13 is eight inches long. Attached to the proximal end of the ancillary infusion line 13 is a three-way plastic stopcock 14. The stopcock 14 is attached to a latex connector 15. The present invention includes the latex connector 15 to allow insertion of more intravenous sets and syringes at that point. The latex material has the ability to seal around inserted needles and exclude the entry of air from insertion points. The proximal inlet of the latex connector 15 is attached by a 0.06 inch internal diameter PVC tube 16, which tube is twelve inches long, to the distal outlet of non-filtered drip chamber 17. Attached to the proximal inlet of the non-filtered drip chamber 17 is a fluid spike connector 18. The fluid spike connector 18 is used to connect an infusate solution bag to the the non-filtered drip chamber 17. Located around the 0.06 inch internal diameter PVC tube 16 is a flow control clamp 19. The flow control clamp 19 is used to restrict or allow passage of fluid from the distal outlet of the non-filtered drip chamber 17. When the fluid spike connector 18 is connected to the infusate solution bag, flow control clamp 19 is closed until slow fluid maintenance is initiated.

The 0.25 inch internal diameter PVC tubing 12 is four inches long, and is connected to the proximal end of a 0.25 inch internal diameter inlet temperature probe connector 20. The inlet temperature probe connector 20 is constructed of a biocompatible metal tube and plastic infusate inlet and outlet ports. It allows non-invasive pre-warmed temperature measurement of the flowing physiologic solutions within, when coupled with a standard temperature probe and monitor. The distal end of the inlet temperature probe connector 19 is attached to the tapered PVC tubing 21 which has a 0.25 inch internal diameter at its proximal end and a 0.375 inch internal diameter at its distal end to receive the proximal end of the heat exchanger. Said tubing is four inches long.

Referring to FIG. 1b, the 0.375 inch internal diameter PVC tubing 21 connects to the proximal infusate inlet of an extracorporeal heat exchanger 22. The extracorporeal heat exchanger 22 is of a type described and illustrated in U.S. Pat. No. 4,177,186 to William Torgeson. It consists of 19 thin-walled, biocompatibly-coated aluminum tubes. Each tube contains biocompatibly coated aluminum rod inserts shaped in a staircase pattern to promote gentle mixing of infusate solution flowing through the rods, and to conduct active heat transfer from separated counter-current water flow about the exterior of the aluminum tubes. The aluminum tubes are encased in a hard plastic shell. Heated water is actively pumped into the plastic shell through the distal connecting port 23, and runs counter-current with the infusate flow. The heated water exits from the proximal water port 24. Water flow cannot exceed 42° Centigrade or 65 pounds per square inch water pressure. The infusate phase pressure limit is 1000 millimeters of mercury. The infusate phase of the heat exchanger unit 22 will initially be primed retrograde in series with the other components of the present invention. The priming solution must be biocompatible.

Attached to the distal infusate outlet of the extracorporeal heat exchanger 22 is the outlet temperature probe connector 25. The outlet temperature probe connector 25 is constructed of a biocompatible metal tube and plastic infusate inlet and outlet ports. It allows non-invasive post-warmed temperature measurement of flowing physiologic solutions exiting the extracorporeal heat exchanger 22, when coupled with a standard temperature probe and monitor.

The distal outlet of the outlet temperature probe connector 25 is attached to a 0.25 inch internal diameter PVC tube 26, which is six inches in length. The 0.25 inch internal diameter PVC tube is attached to the proximal inlet of a 1.70 micron pore size filtered drip chamber 27. The filtered drip chamber 27 is a pliable plastic reservoir containing a 170 micron mesh filter 28 within. It possess no ancillary infusion line. It functions as a final gross microaggregate filter. The distal outlet of the filtered drip chamber 27 is attached to 0.25 inch internal diameter PVC tubing 29 which is 18 inches in length. The 0.25 inch internal diameter PVC tubing 29 is attached to a rigid plastic male perfusion adaptor tip 30. The male perfusion adaptor tip 30 has a 0.25 inch internal diameter, and attaches to the female receptacle of a vein catheter 31. The vein catheter 31 has an internal diameter of at least 14-gauge. The vein catheter 31 is used to penetrate the venous access site.

Before the vein catheter 31 is connected, a temporary spike connector 32 is attached to the male adaptor tip 30. The temporary spike connector 32 connects the present invention to a priming solution bag. After the temporary spike connector 32 is connected to the priming solution bag, retrograde priming of the present invention is performed by inverting the apparatus using aseptic technique. When retrograde priming is accomplished, the temporary spike connector 32 is disconnected from the male perfusion adaptor tip 30 and discarded. The vein catheter 31 is then connected to the male perfusion adapter tip 30, and the present invention is ready for use. The vein catheter 31 should be inserted into the patient's central venous blood pathway. The tube clamps 5 and the flow control clamp 19 are then selectively opened allowing the flow of physiologic solutions to the patient.

I claim:

1. A pump free intravenous set for the rapid infusion of physiologic solutions to treat a patient in hypovolemic shock comprising an infusion line having means at its distal end for connecting the line to a venous pathway of the patient, inlet means mounted on the proximal end of the infusion line for connecting the line to a source of physiologic solution at a temperature below normothermic temperature, and a heat exchanger disposed in the infusion line through which the solution flows for heating the solution to place it a normothermic temperature, said infusion line, inlet means, means on the distal end of the line and the heat exchanger being sized to recieve and discharge said solution at a rapid rate to restore and maintain the normal circulating blood volume of a patient in hypovolemic shock, in response to a pressure head established by the difference in height of the proximal and distal ends of the infusion line.

2. A pump free intravenous set as defined in claim 1 wherein
air embolism guard means are provided in the line for preventing an air bolus from being introduced into the patient from the line.

3. A pump free intravenous set as defined in claim 1 wherein
said inlet means includes a Y-connector on the proximal end of line having a pair of inlet arms for connecting the line to two sources of of physiologic solutions.

4. A pump free intravenous set as defined in claim 3 wherein
tube clamps are provided in each of the inlet arms.

5. A pump free intravenous set as defined in claim 4 wherein
an additional tube clamp is provided in the line distally of the Y-connector, said tube clamps enabling the user to delineate between the two sources of physiologic solutions and to control the flow rate from each source.

6. A pump free intravenous set as defined in claim 1 wherein
an ancillary administration set is connected to the line distally of the Y-connector for infusing drugs and other physiologic solutions into the solution in the line at a slower rate than that of the blood products.

7. A pump free intravenous set as defined in claim 1 wherein
said infusion line, inlet means and heat exchanger are sized to receive crystalloids and blood products and discharge them at a rate of approximately 800 milliliters to 1500 milliliters per minute.

8. A pump free intravenous set as defined in claim 1 wherein
said infusion line, inlet means and heat exchanger are sized to receive packed red blood cells and discharge them at a rate of approximately 800 milliliters per minute.

9. A pump free intravenous set as defined in claim 1 wherein
said infusion line, inlet means and heat exchanger are sized to receive whole blood and discharge it at a rate of approximately 1000 milliliters per minute.

10. A pump free intravenous set as defined in claim 2 wherein
said inlet means includes a Y-connector on the proximal end of line having a pair of inlet arms for connecting the line to two sources of physiologic solutions, and tube clamps provided in each of the inlet arms.

11. A pump free intravenous set as defined in claim 10 wherein
said infusion line, inlet means and heat exchanger are sized to receive crystalloids and blood products and discharge them at a rate of approximately 800 milliliters to 1500 milliliters per minute.

12. A pump free intravenous set as defined in claim 10 wherein
said infusion line, inlet means and heat exchanger are sized to receive packed red blood cells and discharge them at a rate of approximately 800 milliliters per minute.

13. A pump free intravenous set as defined in claim 10 wherein
said infusion line, inlet means and heat exchanger are sized to receive whole blood and discharge it at a rate of approximately 1000 milliliters per minute.

14. A pump free intravenous set as defined in claim 10 wherein
said infusion line, inlet means and heat exchanger are sized to receive packed red blood cells and discharge them at a rate of approximately 800 milliliters per minute.

* * * * *